United States Patent [19]
Cole

[11] Patent Number: 5,755,250
[45] Date of Patent: May 26, 1998

[54] MANIFOLD AND VALVE ASSEMBLY FOR A SMOKE/POLLUTION DETECTION SYSTEM

[75] Inventor: Martin Terence Cole, Keysborough, Australia

[73] Assignee: I.E.I. Pty. Ltd., Victoria, Australia

[21] Appl. No.: 313,197

[22] PCT Filed: May 10, 1993

[86] PCT No.: PCT/AU93/00208
  § 371 Date: Nov. 8, 1994
  § 102(e) Date: Nov. 8, 1994

[87] PCT Pub. No.: WO93/23736
  PCT Pub. Date: Nov. 25, 1993

[30] Foreign Application Priority Data

May 11, 1992 [AU] Australia .................. PL 2381

[51] Int. Cl.⁶ .................................... F16K 17/36
[52] U.S. Cl. ...................... 137/78.5; 137/80; 251/230
[58] Field of Search .............. 137/78.5, 80; 251/230

[56] References Cited

U.S. PATENT DOCUMENTS

| | | | |
|---|---|---|---|
| 1,856,350 | 5/1932 | Metcalf | 251/230 |
| 1,960,515 | 5/1934 | Shield | 251/230 |
| 4,263,930 | 4/1981 | McCabe | 137/80 |
| 4,800,804 | 1/1989 | Symington | 137/80 |
| 5,022,426 | 6/1991 | Fischer | 251/230 |

FOREIGN PATENT DOCUMENTS

| | | | |
|---|---|---|---|
| 3024199 | 1/1982 | Germany | 137/78.5 |
| 2243475 | 10/1991 | United Kingdom . | |

*Primary Examiner*—A. Michael Chambers
*Attorney, Agent, or Firm*—Learman & McCulloch

[57] ABSTRACT

A manifold valve assembly for use in a smoke/pollution detection system in which gas is drawn from a plurality of zones under surveillance and delivered to a smoke/pollution detector. The assembly has a manifold provided with a plurality of inlet ports communicating with the zones and an outlet communicating with the detector. A valve within the housing is reciprocable between a first position in which the outlet communicates with all of said inlet ports and a second position in which only one of said inlet ports communicates with the outlet. The valve is rotated incrementally in response to its reciprocation to enable each of the inlet ports to communicate with the outlet successively.

11 Claims, 6 Drawing Sheets

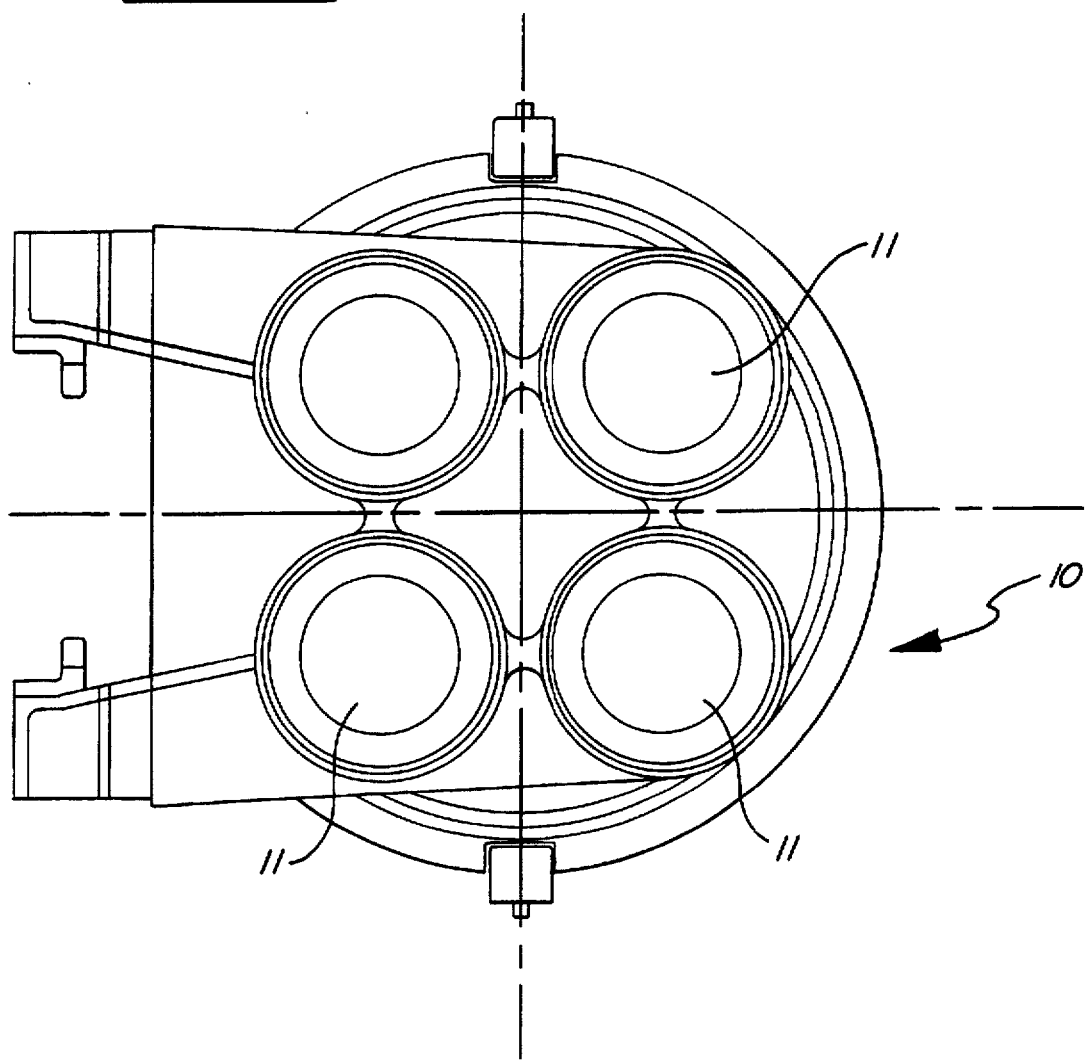

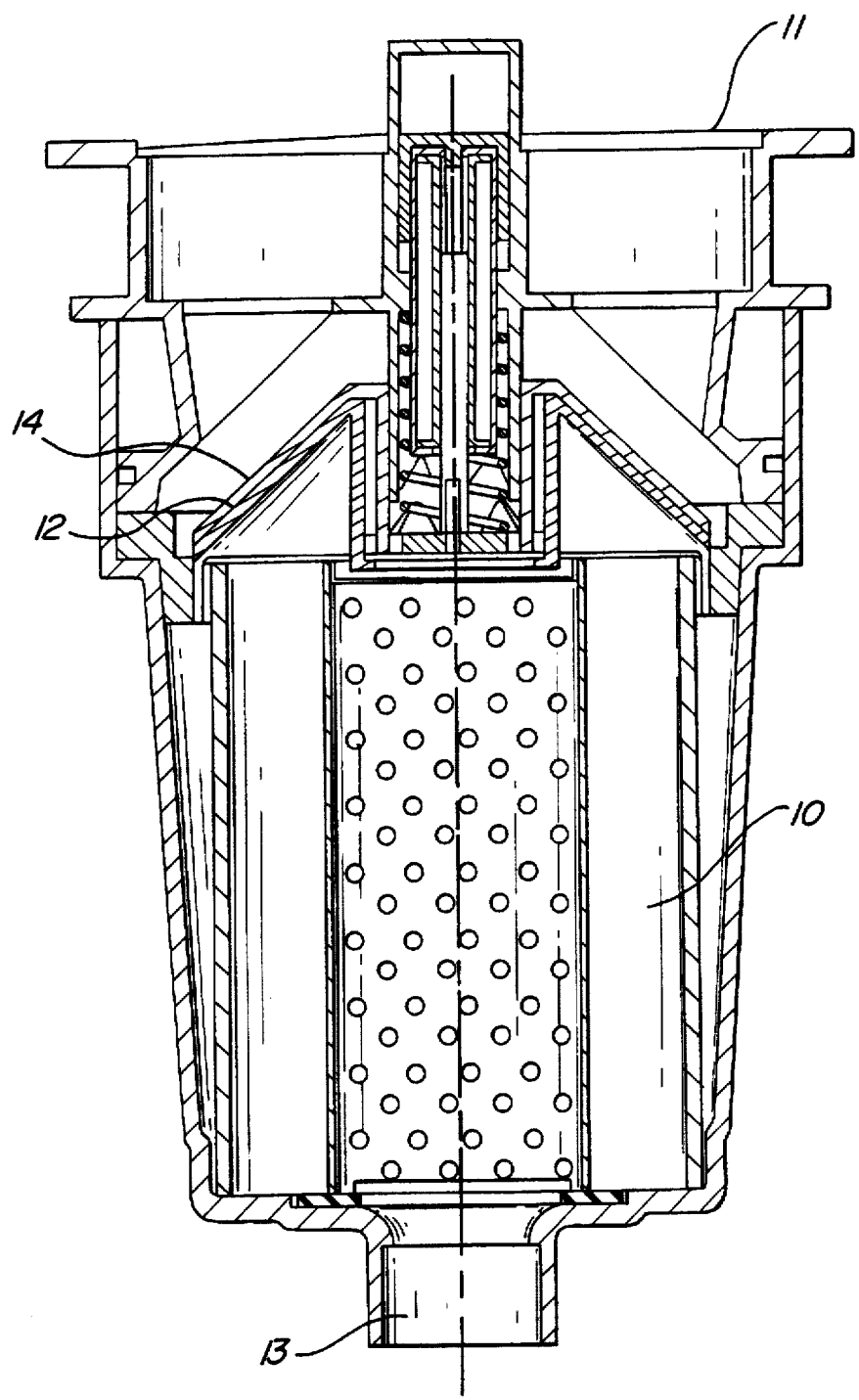

MANIFOLD AND VALVE ASSEMBLY FOR A SMOKE/POLLUTION DETECTION SYSTEM

The present invention relates to a pollution/smoke manifold and valve assembly for use in detection apparatus incorporating an aspirated gas reticulation system connected to a large number of sampling points in which gas from a number of monitored spaces is drawn for testing.

It is normal in such systems for the pipe reticulation system to be jointed at a manifold which incorporates a dust filter prior to exposure of the gas to smoke/pollution detection equipment in a sampling chamber.

A known multi-port manifold preferably includes four equally spaced ports receiving gas samples carried to the ports by a pipe reticulation system.

A search of prior art records reveal several attempts at early warning techniques by way of identifying the specific area or zone from which pollution is being sourced.

Australian Patent No. 624097 relates to a fire alarm system including a plurality of slave fire detectors and a master detector to transmit a signal to a central receiving unit.

U.S. Pat. No. 2,660,052 (Uhl) relates to testing of successively withdrawn samples from a plurality of sources for testing and purging the system with clean air to avoid contamination between sources. This is a continuous process.

U.S. Pat. No. 1,755,834 (Marr) provides for several observation cabinets allowing for visual determination of those cabinets through which smoke is actually present.

U.S. Pat. No. 3,678,487 (Ludewig) discloses a rotary selector valve provided for continuously drawing off samples from zones and subjected to detection apparatus.

French Patent No. 2670010 (Cerberus) discloses detection devices in each supply line from different zones.

U.S. Pat. No. 3,678,488 (Skala) discloses a condensate nuclei monitor which is selectively switched from one zone to another to monitor condensate in each zone respectively with individual adjustment of sensitivity for each zone.

Because the air samples may be drawn from a relatively large area in a building or even from separate buildings, it is desirable in an early warning smoke/pollution detection system for early identification of the specific area or zone from which the smoke/pollution is sourced. This can be achieved by identifying the specific pipe or pipes attached to the manifold that are carrying smoke/polluted air and thereby narrows the search for the potential fire or fire. The above-mentioned prior specifications make an attempt at such early identification and localisation. Such identification will also enable utilisation of a monitoring system in a number of small discrete independently located areas, the individual size of which may not justify their own individual detection system.

It is also desirable that the apparatus achieving these aims is of a low power consumption and has low maintenance requirements.

It is an objective of the present invention to provide in a smoke/pollution detection apparatus a manifold valve device useful in quick identification of a zone in which smoke/pollution is detected.

There is provided according to the present invention, for use in a smoke/pollution detection apparatus, a manifold valve device adapted to receive gas/air drawn from a plurality of zones under surveillance through a reticulation pipe system comprising a plurality of pipes communicating with said zones, said manifold valve device being connected to said plurality of pipes receiving said gas/air, valve means selectively closing none or all but one of the inlet ports to the inlet valve device, the arrangement being such that the locality of the zone of any detected smoke/pollution can be quickly identified, wherein all ports to the manifold valve apparatus remain open in normal circumstances such that all monitored zones remain coupled to the detector and the manifold means is inoperative drawing negligible or no power until such time as smoke/pollution is detected to activate said manifold valve device.

In a further aspect of the invention, there is provided a manifold valve system for use in a smoke/pollution detection apparatus in which gas/air is drawn from a plurality of areas to a location adjacent to the manifold apparatus in which the manifold apparatus includes a plurality of inlet ports each connected to one of said plurality of zones by a gas/air conduit for receiving said gas/air and rotary valve means for selectively closing all or all but one of the inlet ports of the manifold apparatus in succession, the arrangement being such that the area source of any detected smoke/pollution can be identified when said smoke/pollution has been detected by said detection apparatus and wherein the valve means remains inactive until such time as said smoke pollution has been detected.

If a predetermined smoke/pollution level is detected, the valve means is activated so that the contents of each of said plurality of pipes emanating from various designated areas are scanned by the detector to identify that or those pipes and therefore the designated areas carrying the polluted gas/air and therefore the area from which the sample is taken.

In a more specific form of the invention the manifold apparatus includes a valve device which is reciprocally and rotationally mounted relative to a plurality of manifold ports in which said valve device includes one port which is adapted to communicate with a different one of said plurality of manifold ports such that a sample is drawn into said manifold one port at a time to enable identification of the origin of any positive sample.

Thus, for example, in a four port manifold when smoke/pollution is detected the valve is actuated and adapted to close three of the ports at any one time so that only one selected port and monitored area is coupled to the detector.

Under normal conditions (that is no positive sampling detected by the detector), the valve means is de-energised and inoperative so that all four ports remain open for the detector to be exposed to all sampled areas and the operation of the valve does not draw any power.

The valve means is preferably solenoid operated and in such an instance the energy consumption must be kept to a minimum where battery operation is used. Thus energy efficiency must be high requiring economy of movement of the valve with low friction losses and furthermore the device draws zero current until a search mode is initiated with activation of the solenoid.

It is preferable that the device is virtually maintenance free for a long period of time of at least two years and preferably up to ten years. In these circumstances it is necessary that lubrication is not required for moving parts or that the parts are sealed against possible dust contamination.

It is also desirable that the design is compact and can be utilised as a replacement part for existing prior art assemblies particularly in the manifold assembly.

Preferably the system operates with an aspirator of low energy and head and therefore the airflow through the manifold, scanner and dust filter must occur with minimal pressure (head) loss. Therefore it is essential that the system is aerodynamically efficient involving minimal deflection or acceleration of the airstream.

The invention will be described in greater detail with reference to the accompanying figures in which FIG. 1 shows a side view of a prior art manifold and a filter.

FIG. 2 is a vertical sectional view showing the manifold scanning arrangement and filter of the present invention.

Figure 1:
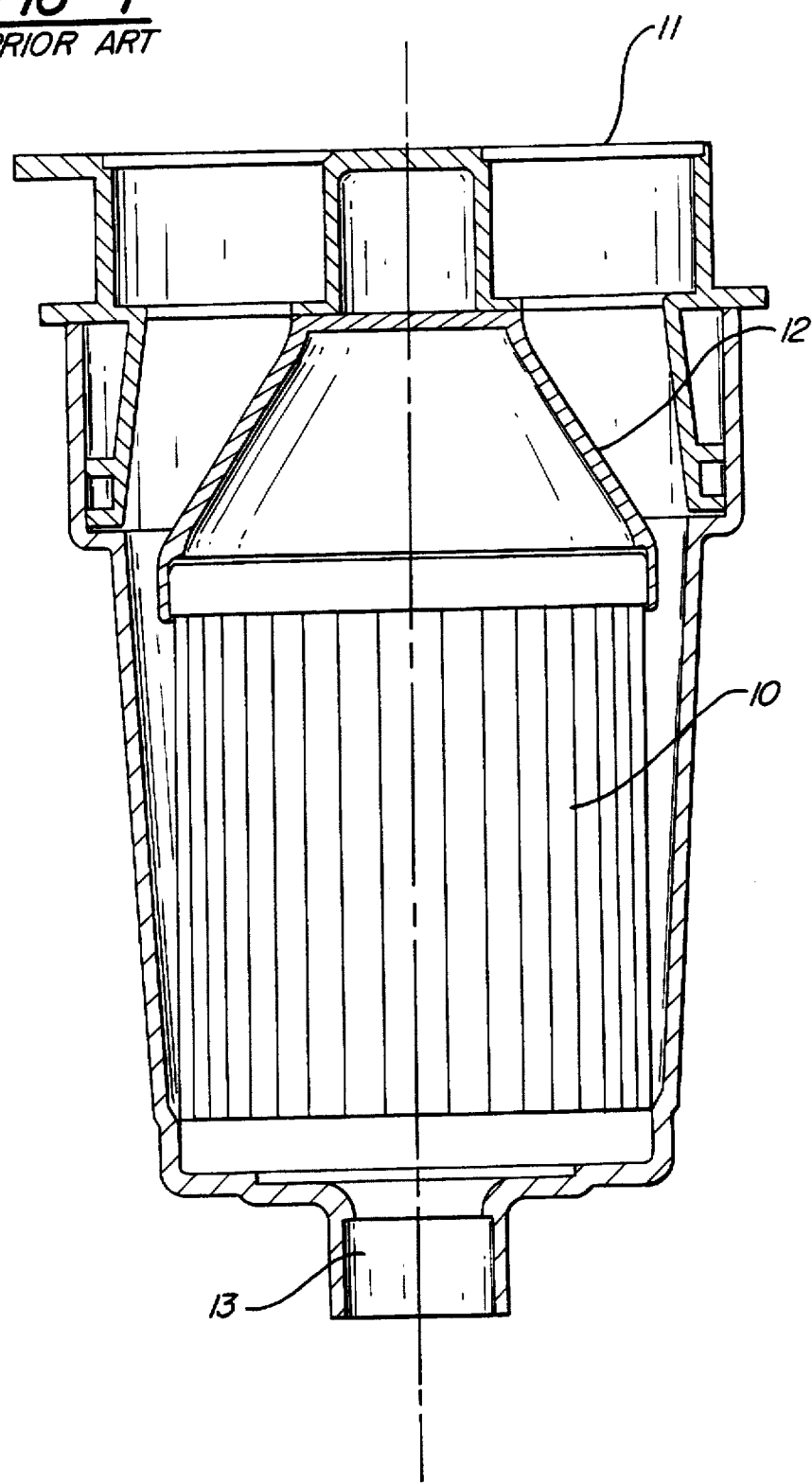
FIG. 1A is a plan view of the manifold/valve arrangement according to the invention.

With reference to FIGS. 1, 1A and 2, the manifold assembly includes four ports 11 leading into a spreader cone area 12 for gently deflecting the airstream from the manifold around the top of the dust filter 10.

With reference to FIG. 2, a matching thin conical bell valve 14 is placed over the spreader cone 12 and in the down position shown in FIG. 2 has no influence on the airflow entering the manifold ports 11 travelling down into the filter 10.

Figure 4:
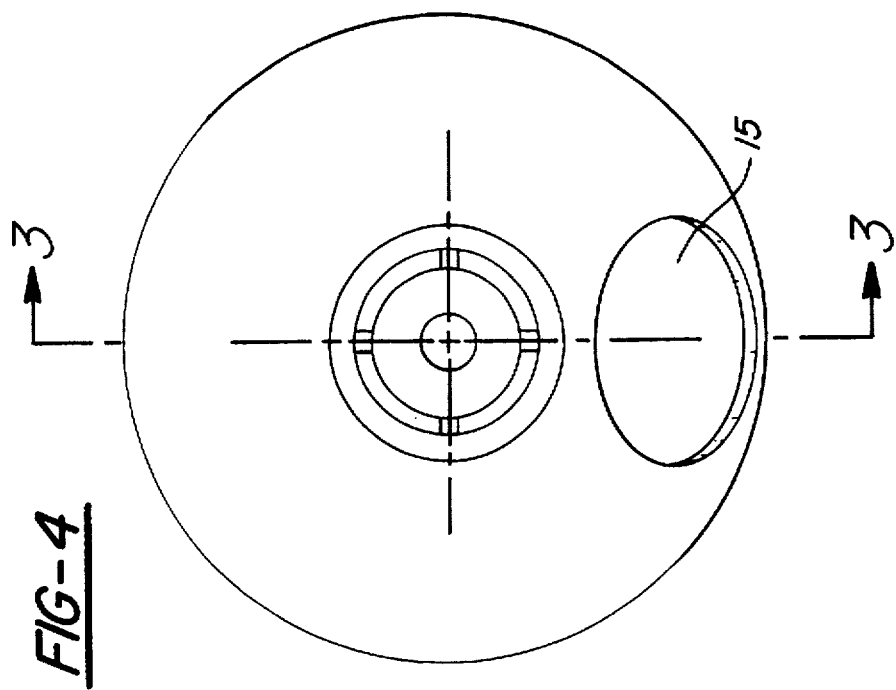
FIG. 4 is a plan view of the valve means.
Figure 3:
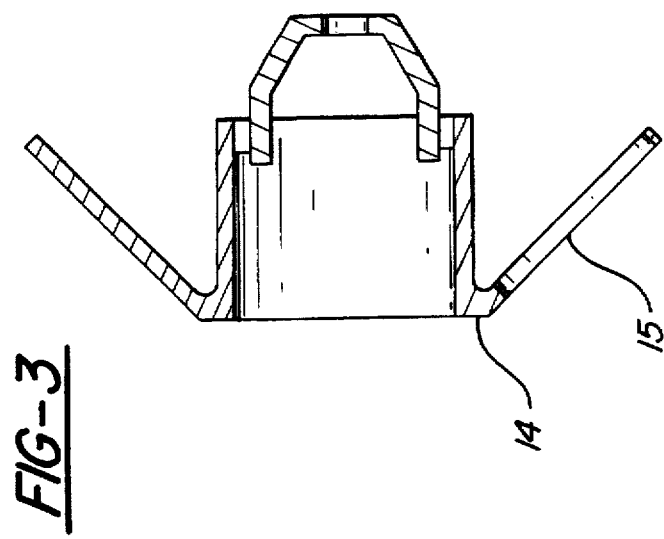
FIG. 3 is a sectional view taken on the line A–A of FIG. 4 and showing the configuration of the valve means.

With reference to FIGS. 3 and 4, the conical bell valve 14 includes a single aperture 15 in its wall.

Figure 6:
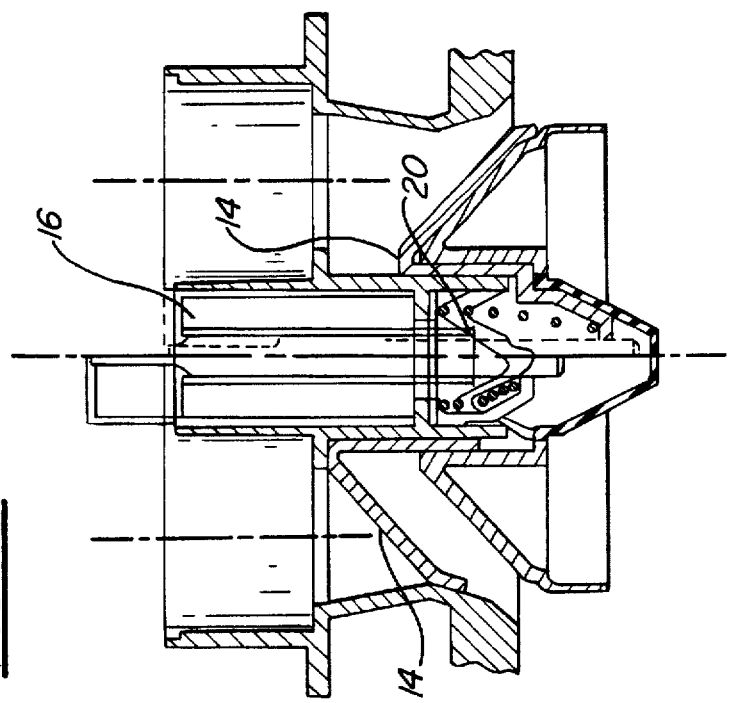
FIGS. 5, 6 and 6A are sectional views showing manual and solenoid operated versions of the rotatable and reciprocal valve means.
Figure 5:
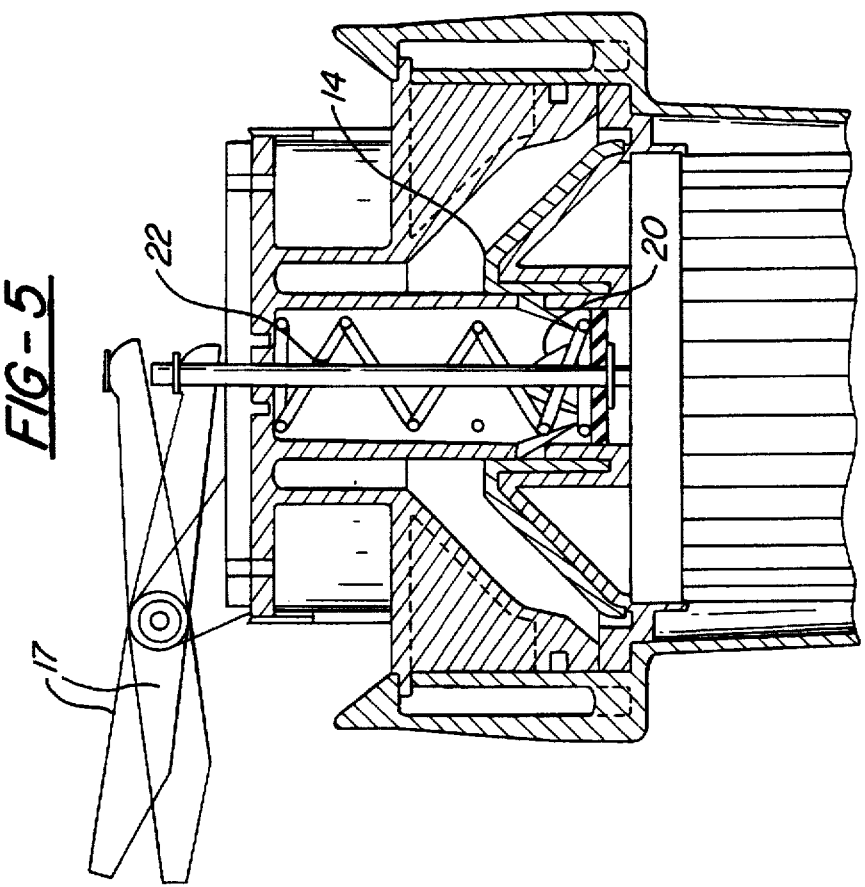
Figure 6A:
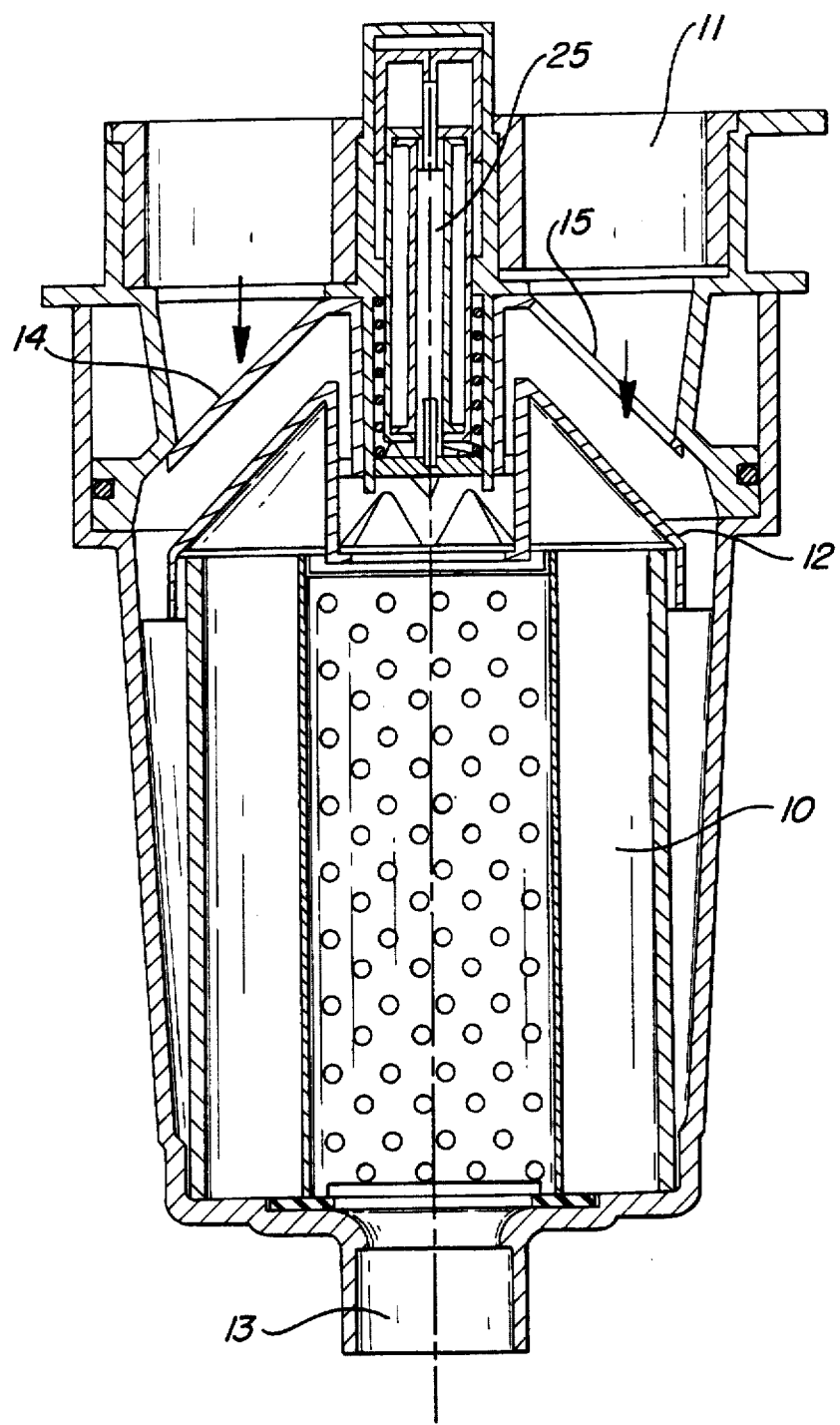

With reference to FIGS. 5, 6 and 6A, the conical bell valve member 14 may be raised axially of the manifold from its lowered position to an upward position as shown in FIGS. 6 and 6A where the aperture 15 is arranged to be aligned with one of the ports 11 in the manifold such that the other three ports in the manifold are blocked.

Thus with the conical bell valve 14 in the raised position sampling into the detector (not shown) will occur from the particular zone that communicates with the open port 11 only.

Axial movement of the conical bell valve is conveniently achieved by means of a solenoid 16 coupled to the valve as shown in FIG. 6 or by a lifting lever 17 coupled to the valve as shown in FIG. 5.

With reference to FIGS. 6 and 6A, rotation or rotary indexing of the conical bell valve 14 sequentially to the next port 11 is achieved by means of a double-acting sawtooth cam 20 which provides a 45° rotation for each solenoid actuated reciprocating movement up and down which results in the necessary 90° total rotation for each reciprocating activation of the solenoid for successive movement of the aperture to the next manifold port 11. FIG. 5 shows the conical bell valve 14 in the lowered position wherein gas is free to enter all four ports 11.

In the case of the manually-operated scanner shown in FIG. 5, the conical bell valve 14 is yieldably retained in its downward fully-open position by means of the biasing spring 22.

It will be appreciated that the entire assembly can, in fact, be operated successfully in any orientation with the spring and solenoid designed to take advantage of any gravitational forces.

In view of the fact that the manifold valve apparatus is normally inactive, no power is drawn and furthermore, there is no mechanical noise from moving parts and the solenoid operator. Furthermore, maintenance and supervision will be kept to a minimum since movement of the parts in the manifold valve arrangement is called upon only during a smoke detection phase.

The solenoid is electrically connected to the output of a smoke detection apparatus (not shown) but examples of which have been previously disclosed in U.S. Pat. Nos. 4,665,311 and 4,670,741 both filed by the same inventor.

I claim:

1. A manifold valve assembly for use in a smoke/pollution detection system of the kind in which gas is drawn from a plurality of zones and passed through said assembly to a smoke/pollution detector, said assembly comprising a housing having a plurality of inlet ports and an outlet, each of said inlet ports being in communication with a different one of said zones and said outlet being in communication with said detector, said assembly including a rotary and axially reciprocable valve operable in a first axial position to enable gas from all of said inlet ports to pass through said outlet and operable in a second axial position to enable gas from only one of said inlet ports to pass through said outlet, means for reciprocating said valve between said first and second axial positions, and indexing means responsive to reciprocation of said valve to rotate said valve incrementally to successive positions in which a different one of said inlet ports communicates with said outlet.

2. The assembly according to claim 1 wherein the means for reciprocating said valve comprises a solenoid coupled to said valve.

3. The assembly according to claim 1 wherein the means responsive to reciprocation of said valve comprises a saw-toothed cam.

4. The assembly according to claim 1 including biasing means yieldably maintaining said valve in said first axial position.

5. The assembly according to claim 1 wherein the means for reciprocating said valve comprises a lifting lever coupled to said valve.

6. A manifold valve assembly for use in a smoke/pollution detection system of the kind in which gas is drawn from a plurality of separate zones and passed through said assembly to a smoke/pollution detector, said assembly comprising a housing having a plurality of inlet ports and an outlet, each of said inlet ports being in communication with a different one of said zones and said outlet being in communication with said detector, said assembly including a rotatably indexable and axially reciprocable valve operable in a first axial position to enable gas from all of said zones to pass through said outlet and operable in a second axial position to enable gas from less than all of said zones to pass through said outlet, means for reciprocating said valve between said first and second axial positions, and indexing means responsive to reciprocation of said valve to rotate said valve incrementally to positions in which different ones but less than all of said inlet ports successively communicate with said outlet.

7. The assembly according to claim 6 including biasing means yieldably maintaining said valve in said first axial position.

8. The assembly according to claim 6 wherein the means for reciprocating said valve comprises a lifting lever coupled to said valve.

9. The assembly according to claim 6 wherein the means for reciprocating said valve comprises a solenoid coupled to said valve.

10. The assembly according to claim 6 wherein said indexing means comprises a saw-toothed cam.

11. The assembly according to claim 6 wherein said housing has a conical wall in which said inlet ports are formed and wherein said valve comprises a conical bell in overlying relation with said conical wall, the cones formed by said conical wall and said conical bell corresponding to one another.

* * * * *